US011213492B2

(12) United States Patent
Afinogenov et al.

(10) Patent No.: US 11,213,492 B2
(45) Date of Patent: Jan. 4, 2022

(54) ANTISEPTIC COMPOSITION COMPRISING UNITHIOL AND DIMETHYLSULFOXIDE, USE OF THE COMPOSITION AND METHOD OF WOUND TREATMENT WITH ITS USE

(71) Applicant: MEDID INNOVATION DEVELOPMENT LTD, Limassol (CY)

(72) Inventors: Gennady Evgenievich Afinogenov, St. Petersburg (RU); Tamaz Omarovich Manasherov, Moscow (LT); Svetlana Konstantinovna Matelo, Mechnikovo (RU); Anna Gennadievna Afinogenova, St. Petersburg (RU)

(73) Assignee: MEDID INNOVATION DEVELOPMENT LTD, Limassol (CY)

( * ) Notice: Subject to any disclaimer, the term of this patent is extended or adjusted under 35 U.S.C. 154(b) by 111 days.

(21) Appl. No.: 16/480,566

(22) PCT Filed: Dec. 5, 2017

(86) PCT No.: PCT/RU2017/000906
§ 371 (c)(1),
(2) Date: Jul. 24, 2019

(87) PCT Pub. No.: WO2018/156052
PCT Pub. Date: Aug. 30, 2018

(65) Prior Publication Data
US 2021/0008006 A1   Jan. 14, 2021

(30) Foreign Application Priority Data

Feb. 22, 2017   (RU) .......................... RU2017106062

(51) Int. Cl.
| | | |
|---|---|---|
| *A61K 31/10* | (2006.01) | |
| *A61P 23/02* | (2006.01) | |
| *A61P 17/02* | (2006.01) | |
| *A61K 31/047* | (2006.01) | |
| *A61K 31/08* | (2006.01) | |
| *A61K 31/14* | (2006.01) | |
| *A61K 31/167* | (2006.01) | |
| *A61K 31/235* | (2006.01) | |
| *A61K 31/498* | (2006.01) | |
| *A61K 31/734* | (2006.01) | |
| *A61K 38/01* | (2006.01) | |
| *A61K 47/20* | (2006.01) | |
| *A61K 47/36* | (2006.01) | |
| *A61K 47/42* | (2017.01) | |

(52) U.S. Cl.
CPC ............ *A61K 31/10* (2013.01); *A61K 31/047* (2013.01); *A61K 31/08* (2013.01); *A61K 31/14* (2013.01); *A61K 31/167* (2013.01); *A61K 31/235* (2013.01); *A61K 31/498* (2013.01); *A61K 31/734* (2013.01); *A61K 38/014* (2013.01); *A61K 47/20* (2013.01); *A61K 47/36* (2013.01); *A61K 47/42* (2013.01); *A61P 17/02* (2018.01); *A61P 23/02* (2018.01)

(58) Field of Classification Search
CPC ........ A61K 31/10; A61K 31/08; A61K 31/14; A61K 31/167; A61K 31/235; A61K 31/498; A61K 38/01; A61K 47/20; A61K 47/36; A61P 23/02; A61P 31/047
See application file for complete search history.

(56) References Cited

U.S. PATENT DOCUMENTS

| | | | |
|---|---|---|---|
| 2,739,922 | A | 3/1956 | Shelanski |
| 3,761,590 | A | 9/1973 | Fox, Jr. |
| 4,614,794 | A | 9/1986 | Easton et al. |
| 2007/0020213 | A1* | 1/2007 | Tamarkin ............... A61K 8/062 424/70.1 |
| 2016/0346294 | A1* | 12/2016 | Sengupta ............. C07D 513/04 |

FOREIGN PATENT DOCUMENTS

| | | |
|---|---|---|
| EP | 0 140 596 A2 | 5/1985 |
| RU | 2 062 113 C1 | 6/1996 |
| RU | 2 088 234 C1 | 7/1996 |
| RU | 2 175 549 C1 | 11/2001 |
| RU | 2 185 155 C2 | 7/2002 |
| RU | 2 284 824 C1 | 10/2006 |
| WO | 2006/121219 A1 | 11/2006 |

OTHER PUBLICATIONS

International Search Report issued in PCT/RU2017/000906, dated Apr. 5, 2018, pp. 1-5.
Written Opinion issued in PCT/RU2017/000906, dated Apr. 5, 2018, pp. 1-6.
Volf, V. et al., "Combined chelation treatment for polonium after simulated wound contamination in rat" Int. J. Radiat. Biol. (Oct. 1995) pp. 395-404, vol. 68, No. 4.
Tarrand, J.J. et al., "Dimethyl Sulfoxide Enhances Effectiveness of Skin Antiseptics and Reduces Contamination Rates of Blood Cultures" Journal of Clinical Microbiology (Feb. 2012) pp. 1552-1557.
Vidal "Bepanthen plus" https://www.vidal.ru/drugs/bepanthen_%20plus__6796, pp. 1-4, accessed on Jun. 20, 2019.
Nazarenko G.I., Sugurova I.Yu.., Glancev S.P. "Wound. Bandage. Patient.", M.: Medicine, 2002, pp. 174-175', published in Russian language.

(Continued)

Primary Examiner — Shirley V Gembeh
(74) Attorney, Agent, or Firm — Tutunjian & Bitetto, P.C.

(57) ABSTRACT

Colloidal antiseptic compositions for treating wounds and/or for use in surgical operations are provided. The compositions form an elastic air- and water-permeable biodegradable film on the wound surface and have antiseptic, hemostatic, anti-inflammatory, wound-healing, and especially anesthetic and antitoxic effects. The compositions include a collagen hydrolysate, one or more salts of alginic acid and one or more antiseptics, and additionally include unithiol and dimethylsulfoxide. The compositions may also optionally include one or more anesthetics.

10 Claims, No Drawings

(56) References Cited

OTHER PUBLICATIONS

Encyclopedia of medicines "Unithiol" https://www.rlsnet.ru/tn_index_id_5313.htm, pp. 1-7, accessed on Jun. 21, 2019, English abstract.

"Manual on Medical Microbiology. General and Sanitary Microbiology. vol. I", Collective of authors, ed. by Labinskaya A.S., Volina E.G., M.: Publishing House BINOM, 2008, p. 465, published in Russian language, together with English language abstract.

MR 2166-80, "Methodological recommendations on the use of behavioral reactions of animals in toxicological studies for the purposes of hygienic rationing", 1980, published in Russian language, pp. 1-49, together with English language abstract.

* cited by examiner

ANTISEPTIC COMPOSITION COMPRISING UNITHIOL AND DIMETHYLSULFOXIDE, USE OF THE COMPOSITION AND METHOD OF WOUND TREATMENT WITH ITS USE

FIELD OF THE INVENTION

The invention pertains to the field of medicine, in particular to the field of wound care and treatment of wound surfaces. Specifically, the invention relates to antiseptic compositions for wound treatment and/or for use in surgical operations, said compositions having antiseptic, hemostatic, anti-inflammatory, wound-healing, anesthetic, and antitoxic effects. In addition, the invention relates to use of said compositions for treating wounds and/or during surgical operations, as well as methods for treating wounds using these compositions.

BACKGROUND OF THE INVENTION

Currently, in medical practice, various compositions are widely used for the wound treatment, said compositions being designed to accelerate healing processes, prevent infection of the wound by microorganisms and to physically protect the wound surface from the environment.

Depending on the location of the wound, its contamination, the nature of the injury and other factors, the prior art discloses technical means and compositions of various types useful for the wound treatment.

In particular, for treating wounds contaminated by microorganisms, formulations in the form of ointments and solutions are widely used, said formulations being based on polyvinylpyrrolidone-iodine complexes (see U.S. Pat. No. 2,739,922 A), having a sufficiently broad spectrum of antimicrobial activity. Examples of such formulations include some well-known such as Betadine and Wocadin. However, use of iodine-based compositions is limited due to possible allergic reactions, as well as in the case of hyperthyroidism.

In the prior art, expensive silver sulfadiazine based ointments are known as well, said ointments being used for treating burn wounds (see U.S. Pat. No. 3,761,590 A). Examples of the formulations based on silver sulfadiazine are Dermazin, Silvadene, Silvederma and Sulfargin. Contraindications to their use are hypersensitivity to sulfanilamide drugs, as well as severe liver and kidney disorders.

In the prior art, a cream Bepanthen-plus is known for the treatment of superficial wounds, which is a homogeneous soft opalescent cream having a white to yellowish color, with a weak characteristic odor. Cream Bepanthen-Plus comprises dexapanthenol and chlorhexidine as active components, as well as auxiliary substances: pantolactone, cetyl alcohol, stearyl alcohol, lanolin, soft white paraffin, liquid paraffin, macrogol stearate and purified water. Cream Bepanthen-plus is not recommended for use in the case of large, deep and heavily contaminated wounds (Electronic reference book of medical formulations "VIDAL", 2016; https://www.vidal.ru/drugs/bepanthen plus 6796).

In addition, in the prior art, a wide range of film dressings is known comprising antimicrobial agents in their adhesive layer. The films comprising iodine and chlorhexidine are widely used for the protection of skin around surgical wounds and in the places of punctures around the central and peripheral venous catheters.

In particular, the prior art discloses an antiseptic wound healing adhesive comprising antiseptic miramistin, ethyl alcohol and BF-6 polymer (see the abstract of RU 2185155 C2). This adhesive has antibacterial and antifungal action, enhances regenerative processes in the wounds and protects clean wounds from infection. At the same time, the antiseptic adhesive comprising miramistin has a number of significant drawbacks, as it contains ethanol and air-impermeable polymer BP-6. The field of its use is limited to minor epidermal damage (scratches, abrasions), i.e. the wounds that do not penetrate the entire thickness of the dermis. An adhesive with miramistin is not used in the treatment of soft tissue wounds.

The prior art also discloses combined sponge dressings combining the positive effects of proteins and polysaccharides in the treatment of wounds: creating an environment for healing (alginates and chitosans) and for forming a matrix for growth of newly formed granulation tissue (collagen).

For example, Algicol is an original domestic spongy bandage comprising 25% to 75% of cross-linked collagen and 75% to 25% of (calcium) alginate, respectively. In order to ensure the antimicrobial properties of the bandage, it can comprise 0.5% to 5% of potassium furagin. It has been found that an increase in the collagen amount in the complex leads to an increase in its stability and structural strength. Inclusion of antiseptics (furagin and shikonin) and anesthetics (trimecaine) in the bandage provides for the preparation of a biologically active composite spongy bandage. Algicol is well-proven in the treatment of infected and purulent wounds, stimulating the process of granulations formation and maturation and providing a moderate antiseptic effect. Presently, Algicol is not produced anymore.

Fibracol is a lyophilized sponge comprising fibers of cross-linked collagen with an addition of 10% of a mixture of calcium-sodium alginic acid salt, similar to those described in U.S. Pat. No. 4,614,794 A. When applied to a wound, the film quickly becomes wet and is easily modeled, while retaining its structural properties. It requires a secondary and pressure bandage and a retention layer. Fibracol is a foreign analogue of Algicol (see 'Nazarenko G. I., Sugurova I. Yu., Glancev S. P. "Wound. Bandage. Patient.", M.: Medicine, 2002, pp. 174-175', published in Russian language).

These wound dressings have a number of disadvantages: they comprise cross-linked collagen that slows biodegradation of the wound coating, which, in turn, reduces the rate of the formation of a matrix for growth of newly formed granulation tissue. In addition, "Algicol" without antiseptic has no antimicrobial activity, and in the presence of furagin and shikonin it only has a weak bactericidal effect.

For the treatment of wounds, two main types (forms) of hydrogel dressings are currently used. One type of such products has a fixed (firmly cross-linked) three-dimensional macrostructure and is an elastic transparent plate of varied thickness. Bandages of this type usually do not change their physical shape during the absorption of wound exudate, although they may swell and increase in volume. The swelling process continues until the gel becomes completely saturated, i.e. an equilibrium is reached between the bandage and the surrounding wound environment.

Products of the second type do not have a fixed structure and are amorphous substances (in particular, gels) capable of swelling upon contact with liquids. As the absorption intensifies, the viscosity of these gels decreases, and they spread over the wound, taking the form of all its depressions. Such an amorphous hydrogel continues to absorb the liquid until it loses all of its cohesive properties and becomes a polymer solution in the wound. The main mechanism of therapeutic action of hydrogels is the creation of a moist environment on the wound under them, thus promoting wound healing.

In stage I of the wound process, the moist environment provides for a stimulation of autolysis and wound cleansing; in stage II, it creates conditions for the growth and maturation of granulations; in stage III, it creates conditions for the formation of a soft and elastic scar.

The ability of amorphous gels to rapidly release biologically active substances (BAS) into the wound medium makes them irreplaceable in the treatment of chronic wounds. The possibilities of obtaining depot-dressings comprising BAS, including antiseptics, from hydrogel coatings, are not fully disclosed. However, it is clear that unless hydrogels having antimicrobial properties are developed, their use on infected and purulent wounds is only possible in a limited variety of cases or should take place alongside a systemic antibiotic therapy.

The mechanism of therapeutic action of hydrogels is associated with their ability to hydrate the wound and absorb wound exudate. An increase in the concentration of hydrolases (collagenases) under hydrogel dressings stimulates necrosis rejection due to autolysis, and involvement of soluble growth factors, interleukins and cytokines on the wound surface promotes migration of keratinocytes and wound epithelization.

One of the gels for wound dressing is Solcoseryl-gel ("Medical drugs", Mashkovsky M. D., 1993, volume 2, p. 139). This formulation comprises 8.3 mg of chemically and biologically standardized deproteinized hemodializate obtained from blood of dairy calves, as well as sodium salt of carboxymethylcellulose, propylene glycol, calcium lactate and parabens E216 and E218. Solkoseril-gel is used for the treatment of slow healing, especially weeping wounds of various origins, thermal, chemical and radiation burns. At the same time, Solcoseryl-gel has a number of disadvantages. It has a low antimicrobial activity, is prone to very rapid biodegradation on the wound surface, easily absorbed into the gel dressing, which leads to a decrease in the antimicrobial and absorbent capacity of the drug, requires more frequent application of the gel and leads to a significant increase in the cost of treatment.

Patent RU 2284824 (C1), fully incorporated herein by reference, discloses an antiseptic composition for use in surgery, which is the closest analogue of the claimed invention. The known composition comprises collagen hydrolysate (50.0 to 80.0 wt %), sodium alginate (1.0 to 10.0 wt %), glycerol (1.0 to 3.0 wt %), benzalkonium chloride (Catapol, 0.5 to 1.0 wt %), dioxidine (0.5 to 2.0 wt %), Poviargol (0.5 to 2.0 wt %), methylparaben (Nipagin, 0.002 wt %), propylparaben (Nipazol, 0.002 wt %) and an aqueous solution of sodium hypochlorite (balance). It has been shown that this composition has a significant antimicrobial effect against the causative agents of infectious complications of wounds (staphylococci, streptococci, gram-negative bacteria, spore-forming and non-spore-forming anaerobes, Candida fungi, etc.), anti-inflammatory and wound-healing properties. It provides for aseptic healing conditions, protects the wound from external mechanical influences, contamination and infection. The combined use of antiseptics having different mechanisms of action leads to a significant antimicrobial effect, and the ratio of biopolymer concentrations (that is, collagen and sodium alginate) ensures the ability to control biodegradation of the adhesive, thus providing an acceleration of wound healing as a result. Important disadvantages of the known composition are the following:

the known composition does not have any antitoxic action with respect to microbial and tissue toxins, the presence of which aggravates the condition of the patient dramatically;

the known composition does not have any anesthetic effect, which reduces its effectiveness in the patients at the time of trauma due to the development of traumatic shock, subsequent disruption of blood circulation in the area of trauma, which in turn leads to additional intoxication of the patient's organism due to the production of toxins by damaged tissues, and an additional deterioration of the condition of the patient.

In the prior art, it is known that in the case of severe mechanical damage, the negative impact of neural pain impulses, endotoxicosis and other factors inevitably adds to the pathological effect of the hemorrhage, thus always making the condition of the patient with a traumatic shock heavier as compared to the "pure" blood loss of equal volume. With further aggravation of the traumatic shock due to the growing deficit in the oxygen delivery to the tissues, the energy production switches to the anaerobic glycolysis pathway, and the body accumulates acidic products (lactic acid, etc.) and toxic substances of several types: toxic amines (histamine, serotonin, prostaglandin), polypeptides (bradykinin, kallidin), enzymes (lysosomal amines), tissue metabolites (electrolytes, adenyl compounds, ferritin). They all inhibit blood circulation, respiration, contribute to the breakdown of antimicrobial barriers and development of irreversible changes in the cells. Metabolic acidosis develops, which plays an important pathogenetic role in the late period of the traumatic shock (stimulation of adrenal medulla function, electrolyte imbalance, increased intravascular fluid volume). Autocatalytic flooding of the body with toxic substances aggravates the crisis of microcirculation, disrupts functions of a number of organs and systems. At the final stage of the traumatic shock, due to the oxygen deficiency, the endotoxicosis, impaired liver and other organs function, irreversible death of cellular structures ("refractory" shock) develops; death of the patient becomes inevitable (Medical Encyclopedia, www.dic.academic.ru).

Despite the large amount of information available in the prior art on various compositions used for wound treatment and/or during surgical operations, there is still a significant demand for new compositions having antiseptic, hemostatic, anti-inflammatory, wound-healing, anesthetic and antitoxic properties in the art.

Therefore an object of the present invention is to provide novel antiseptic compositions capable of overcoming the disadvantages of the compositions known from the prior art, in particular, additionally exhibiting antitoxic and anesthetic properties.

SUMMARY OF THE INVENTION

To solve the above technical problem, the inventors have developed new colloidal antiseptic compositions for treating wounds and/or for use in surgical operations, said compositions forming an elastic air- and water-permeable biodegradable film on the wound surface and exhibiting antiseptic, hemostatic, anti-inflammatory, wound-healing, and especially anesthetic and antitoxic effects.

The compositions according to the invention comprise a collagen hydrolysate, one or more salts of alginic acid and one or more antiseptics, and are characterized in that they additionally comprise unithiol and dimethylsulfoxide.

The compositions according to the invention may also optionally comprise one or more anesthetics, preferably one or more local anesthetics.

In addition, the invention relates to use of the compositions according to the invention as an agent for wound treatment.

The present invention also relates to methods for treating wounds using the compositions according to the invention, said method comprising the step of applying the composition according to the invention to a wound surface.

Other aspects of the present invention will be apparent to those skilled in the art from the following description and from the appended claims.

The inventors have found that the compositions according to the invention form an elastic air- and water-permeable biodegradable film on the wound surface, which, if necessary, is easily removed by water or saline, provides an advantageous combination of antiseptic, hemostatic, anti-inflammatory, wound-healing, anesthetic, and antitoxic properties and has a significant antimicrobial effect against various pathogens causing infectious wound complications.

The compositions according to the invention are characterized by an optimal film formation time, controlled biodegradation rate, have good adhesion to the skin, mucous membranes and tissues, and provide additional fixation of the dressings on the skin surface around the wound.

In particular, an advantageous property of the compositions according to the invention is their ability to exert a significant detoxification effect when applied to the wound surface, which can lead to a significant acceleration of the healing process and an improvement in the general condition of the patient.

DETAILED DESCRIPTION OF THE INVENTION

The term "wound" in the present invention is understood as a trauma of any part of a human or animal body with a violation of the skin and/or mucous membrane integrity. Preferably, in the present invention, the "wound" is meant to represent a damage caused by a physical impact, however, the damage caused by other damaging factors is also included in the meaning of the "wound" in the present invention.

The wounds in the present invention include both accidental wounds (domestic and industrial injuries, injuries from accidents and natural disasters, etc.), and wound that are inflicted deliberately (such as wounds from surgical operations, as a result of fighting and/or unlawful actions of a third party, etc.).

Wounds can be classified as aseptic, i.e. applied in sterile conditions, and infected. Infected wounds can be primarily infected, i.e. caused by a non-sterile object, and infected after the injury occurred (secondary infection).

The term "collagen hydrolysate" in the present invention is understood to mean a product of enzymatic hydrolysis of collagen. Collagen hydrolysate is typically obtained from the skin of pigs, cattle, from fish skin, bones and cartilage, etc. In the present invention, collagen hydrolysate of any origin or a mixture of such hydrolysates may be used. For example, collagen hydrolysate derived from bovine skin, fish collagen hydrolysate or mixtures thereof can be used in the compositions according to the invention.

The term "alginic acid salts" in the present invention includes pharmaceutically acceptable salts of alginic acid, such as, for example, sodium alginate, potassium alginate and calcium alginate. The salts of alginic acid are not limited in any particular way in the present invention, provided these salts are capable of forming viscous colloidal solutions in water.

Unithiol, in the present invention, means sodium salt of 2,3-bis(sulfanyl)propane-1-sulfonic acid (2,3-bis(sulfanyl) propane-1-sulfonic acid may also be referred to as unithiol).

Unithiol is known in the prior art as a chelating agent capable of binding via its active sulfhydryl groups to arsenic compounds and salts of heavy metals in blood and tissues, thus inactivating them and facilitating their removal from the body ("Encyclopedia of medicines", https://www.rlsn-et.ru/tn_index_id_5313.htm, published in Russian). The antidote and detoxication action of unithiol is ensured by the presence of two sulfhydryl groups (—SH), capable of forming complex bonds, which can form a fairly stable complex with heavy metals, thus having an antidote effect. Use of unithiol as an antidote in the case of arsenic compounds and heavy metal salts poisoning results in binding of these heavy metals in the blood and tissues and in restoration of the function of the affected enzyme systems of the body. The same mechanism of action manifests when treating hepatocerebral dystrophy (Wilson disease) using unithiol, in which case, among other symptoms, there are abnormalities of the copper exchange and copper accumulation in the subcortical nuclei of the brain. Compared with its analogue, dimercaprol or 2,3-bis(sulfanyl)propan-1-ol, unithiol is less toxic, and its good solubility in water makes it more convenient for use and provides for its rapid absorption. Unithiol is included in the list of vital and essential drugs. The main indications for its use are acute and chronic poisoning by organic and inorganic compounds of arsenic, mercury, gold, chromium, cadmium, cobalt, copper, zinc, nickel, bismuth, antimony; intoxication with cardiac glycosides, hepatocerebral dystrophy (Wilson's disease). It is also used to bind products of incomplete oxidation of ethyl alcohol causing hangover. Use of unithiol in acute poisoning does not exclude other therapeutic measures (gastric lavage, inhalation of oxygen, administration of glucose and others). In addition, use of unithiol has been reported in the case of some other poisonings and diseases. There are data on the beneficial effect of unithiol in diabetic polyneuropathies. Perhaps this is due to the fact that patients with diabetes mellitus have a reduced content of sulfhydryl groups in the blood.

To the best of the inventors knowledge, unithiol has not previously been used as an antidote to microbial and tissue toxins, and has not been used in the wound treatment.

In the present invention, the expressions "comprises" and "includes" and their derivatives are used interchangeably and are understood as being non-limiting, i.e. allowing for a presence/use of other components, stages, conditions, etc., in addition to those listed explicitly. On the contrary, the expression "consists of", "is composed of" and their derivatives are intended to mean that the components, stages, conditions and the like listed after that are exhaustive.

In the present invention, when a range of possible values is provided for any value, it is to be understood that the upper and lower limits of the range are also included in the scope of the invention. It should also be understood that all the sub-ranges within the provided ranges are also included in the scope of the present invention as if they were disclosed explicitly. In case several ranges of possible values are provided for any value, all the ranges obtained by combining different endpoints of these ranges are also included in the present invention as if they were disclosed explicitly.

In case any features of the invention are disclosed herein for one of possible embodiments, the same features may also be used in all other embodiments of the invention, provided it does not contradict the spirit and technical sense of the invention.

With the exception of the experimental part of the description, all numerical values defining any quantities and conditions in the present invention are approximations and should be read as preceded by the word "about", even when said word is not directly mentioned. On the contrary, all numerical values recited in the experimental part of the description are given as precisely as possible. However, it should be understood that any experimentally found value comprises a certain error due to its very nature. Thus, all the numerical values given in the experimental part of the description should be read with taking into account the existence of said experimental error and, at the very least, the number of the available significant digits and standard rounding techniques.

The compositions according to the invention comprise a collagen hydrolysate, one or more salts of alginic acid and one or more antiseptics, and are characterized in that they additionally comprise unithiol and dimethylsulfoxide.

Not wishing to be bound by any theory, the inventors believe that unithiol (2,3-bis(sulfanyl)propane-1-sulphonate), when the composition according to the invention is applied to the wound surface, binds microbial and tissue toxins and thus directly exerts detoxification effect in the wound. This effect is highly unexpected, since the prior art has not previously reported the ability of unithiol to bind microbial and tissue toxins. Moreover, nothing was known about the ability of unithiol to bind microbial and tissue toxins when applied topically to the wound surface. In the present invention, the inventors have shown that use of unithiol in an antimicrobial composition for treating wounds results in a significant acceleration of wound healing processes. In addition, the inventors have surprisingly found that use of unithiol in an antimicrobial composition for treating wounds leads to a decrease in the microbial contamination of the wound.

The amount of unithiol in the compositions according to the invention may vary depending on the contamination of the wound, the nature of the damage, the intensity of the inflammatory process, and other factors. A person skilled in the art, on the basis of his/her own knowledge, using the prior art and routine experiments, will be able to easily determine the amount of unithiol to be used in each particular case. In some embodiments, the composition according to the invention may comprise about 0.1 to about 10 wt % of unithiol, based on the total weight of the composition. In some embodiments, the amount of unithiol in the composition according to the invention may be about 0.5 to about 9 wt %, about 1 to about 8 wt %, about 1 to about 7 wt %, about 2 to about 7 wt %, about 3 to about 6 wt %, preferably about 3 to about 5 wt %, or about 4 to about 5 wt %, based on the total weight of the composition.

The compositions according to the invention also comprise dimethylsulfoxide. Not wishing to be bound by any theory, the inventors believe that dimethylsulfoxide, when used in the compositions of the invention, contributes to the penetration of the active ingredients of the composition into the skin and soft tissues, thereby providing for an enhancement of efficacy of the active components in the composition.

The amount of dimethylsulphoxide in the compositions according to the invention may vary in a wide range. A person skilled in the art, on the basis of his/her own knowledge, the prior art, and routine experiments, will be able to easily determine the amount of dimethylsulphoxide to be used in each particular case. In some embodiments, the composition according to the invention may comprise about 0.05 to about 5 wt % of dimethylsulfoxide, based on the total weight of the composition. In some embodiments, the amount of dimethylsulphoxide in the composition according to the invention may be about 0.07 to about 3 wt %, about 0.1 to about 2 wt %, about 0.1 to about 1 wt %, about 0.2 to about 0.8 wt %, from 0.3 to about 0.7 wt %, from 0.4 to about 0.6 wt %, preferably about 0.5 wt %, based on the total weight of the composition.

The amounts of a collagen hydrolysate and alginic acid salts in the composition according to the invention may vary in wide ranges and are determined on the base of practical usability reasoning, such as by the desired thickness and elasticity of the resulting film, its air and water permeability, biodegradability, film formation time, and the like. A suitable amount of collagen hydrolysate and alginic acid salts can be determined by a person skilled in the art based on the general knowledge and the prior art using routine experiments.

In some embodiments, the amount of a collagen hydrolysate in the composition according to the invention may be about 40 to about 80 wt %, based on the total weight of the composition. In some embodiments, the amount of the collagen hydrolysate in the composition according to the invention may be about 45 to about 80 wt %, about 50 to about 80 wt %, about 50 to about 75 wt %, about 50 to about 70 wt %, about 50 to about 65 wt %, about 50 to about 60 wt %, or about 50 to about 55 wt %, based on the total weight of the composition.

In some embodiments, the amount of one or more salts of alginic acid in the composition according to the invention may be about 1 to about 10 wt %, based on the total weight of the composition. In some embodiments, the amount of the one or more salts of alginic acid in the composition according to the invention may be about 1.5 to about 9 wt %, about 2 to about 8 wt %, about 2 to about 7 wt %, about 2.5 to about 7 wt %, about 3 to about 6 wt %, or about 4 to about 5 wt %, based on the total weight of the composition.

In one embodiment, a preferred salt of alginic acid suitable for use in the compositions according to the invention is sodium alginate.

As indicated above, the compositions according to the invention comprise one or more antiseptics. It is well known to one of ordinary skill in the art, from the general knowledge and the prior art, what antiseptics can be used in wound treatment compositions and wound dressings. In particular, the choice of antiseptics may depend on the type of suspected infection agents. If it is necessary to obtain a wide spectrum of antimicrobial activity against a wide range of infectious agents, it is preferable to use several antiseptics in the composition according to the invention, said antiseptics having different mechanisms of action, thus resulting in a significant antimicrobial effect against most of the main infectious agents known to cause wound complications (staphylococci, streptococci, gram-negative bacteria, spore-forming and non-spore-forming anaerobes, fungi of the Candida genus, etc.). For example, the following antiseptics are exemplary antiseptics suitable for use in the present invention: oxyquinoline derivatives, such as dioxidine (hydroxymethyl quinoxylindioxide); quaternary ammonium compounds, such as miramistin and benzalkonium chloride; silver-based antiseptics, such as poviargol (silver nanoclusters stabilized with low molecular weight polyvinylpyrrolidone, http://sktb-technolog.ru/category/pharmaceutics/poviargolum; "ARGAKOL. Collected materials on the use of wound coating", ed. by Afinogenov G. E., St. Petersburg, "Borey Art" Publishing House, 2008, p. 30; see also RU 2088234 C1, all published in Russian language); biguanides, such as chlorhexidine, polyhexamethylene-biguanide derivatives; bisphenols, such as triclosan; parabens, such as methylparaben and propylparaben; alcohols such as glycerol; chlorine compounds such as sodium hypochlorite;

iodine compounds such as povidone-iodine (iodine complex with polyvinylpyrrolidone) and the like.

The amount of antiseptic(s) used in the compositions according to the invention depends on the antiseptic(s) type, the type of pathogen, the nature of the wound, and other factors. A person skilled in the art, on the basis of his/her own knowledge, the prior art and routine experiments, can easily determine the amount of antiseptic(s) to be used in each particular case. In some embodiments, the amount of antiseptic(s) in the composition according to the invention may be about 0.01 to about 20 wt %, based on the total weight of the composition. In some embodiments, the amount of antiseptic(s) in the composition according to the invention may be about 0.05 to about 15 wt %, about 0.1 to about 12 wt %, about 0.1 to about 10 wt %, about 0.15 to about 10 wt %, about 0.2 to about 9 wt %, about 0.3 to about 8 wt %, about 0.4 to about 7 wt %, about 0.5 to about 6 wt %, about 0.5 to about 5 wt %, about 0.6 to about 5 wt %, about 0.7 to about 4 wt %, about 0.8 to about 3 wt %, or from 1 to about 2 wt %, based on the total weight of the composition.

In one preferred embodiment, the composition according to the invention comprises dioxidine as an antiseptic or one of the antiseptics. The amount of dioxidine in the composition according to the invention can be about 0.1 to about 10 wt %, for example about 0.2 to about 7 wt %, such as about 0.5 to about 5 wt %, such as about 1 to about 4 wt %, such as about 1 to about 3 wt % or about 1.5 to about 2 wt %, based on the total weight of the composition.

In one preferred embodiment, the composition according to the invention comprises poviargol as an antiseptic or one of the antiseptics. The amount of poviargol in the composition according to the invention can be about 0.1 to about 10 wt %, for example about 0.2 to about 7 wt %, such as about 0.5 to about 5 wt %, such as about 1 to about 4 wt %, such as about 1 to about 3 wt %, or about 1.5 to about 2 wt %, based on the total weight of the composition.

In one preferred embodiment, the composition according to the invention comprises benzalkonium chloride as an antiseptic or one of the antiseptics. The amount of benzalkonium chloride in the composition according to the invention may be about 0.01 to about 2 wt %, for example about 0.02 to about 1 wt %, such as about 0.05 to about 0.7 wt %, such as about 0.05 to about 0.5 wt %, such as about 0.07 to about 0.5 wt %, such as about 0.1 to about 0.3 wt %, preferably about 0.15 wt %, based on the total weight of the composition.

In one preferred embodiment, the composition according to the invention comprises glycerol, as an antiseptic or one of the antiseptics. The amount of glycerol in the composition according to the invention may be about 0.1 to about 15 wt %, for example about 0.5 to about 10 wt %, for example about 1 to about 8 wt %, for example about 1.5 to about 5 wt %, for example about 2 to about 3 wt %, preferably about 2.5 wt %, based on the total weight of the composition.

In one preferred embodiment, the composition according to the invention comprises methylparaben as an antiseptic or one of the antiseptics. The amount of methylparaben in the composition according to the invention may be about 0.001 to about 2 wt %, for example about 0.01 to about 1 wt %, such as about 0.05 to about 0.5 wt %, such as about 0.05 to about 0.2 wt %, such as about 0.07 to about 0.15 wt %, preferably about 0.1 wt %, based on the total weight of the composition.

In one preferred embodiment, the composition according to the invention comprises propylparaben as an antiseptic or one of the antiseptics. The amount of propylparaben in the composition according to the invention may be about 0.001 to about 2 wt %, for example about 0.005 to about 1 wt %, such as about 0.01 to about 1 wt %, such as about 0.01 to about 0.5 wt %, such as about 0.05% to about 0.1 wt %, based on the total weight of the composition.

In one preferred embodiment of the invention, the composition according to the invention comprises a combination of dioxidine, poviargol, benzalkonium chloride, glycerol, methylparaben and propylparaben, taken in the amounts indicated above, as an antiseptic.

The composition according to the invention may additionally comprise one or more anesthetics to reduce the pain syndrome threshold and improve microcirculation in the blood vessels. An addition of anesthetic(s) into the composition according to the invention can prevent the onset of a traumatic shock, subsequent circulatory disorders in the area of injury, which, in their turn, may lead to additional intoxication due to the production of toxins by damaged tissues and additional worsening of the condition of the affected human or animal. One skilled in the art is well aware of anesthetics that can be used in wound treatment compositions and dressings. For example, lidocaine, trimekain, tetracaine, novocaine, etc, may be listed as non-limiting examples of the anesthetics suitable for use in the compositions according to the invention. In one embodiment, a preferred anesthetic suitable for use in the compositions according to the invention is lidocaine.

The amount of anesthetic(s) in the compositions according to the invention may vary within a wide range according to the anesthetic type, and the nature and the contamination of the wound, the intensity of inflammation and other factors. A person skilled in the art, on the basis of his/her own knowledge, the prior art and routine experiments, can easily determine the amount of anesthetic(s) to be used in each particular case. In some embodiments, the amount of anesthetic(s) in the composition according to the invention may be about 0.01 to about 10 wt %, based on the total weight of the composition. In some embodiments, the amount of anesthetic(s) in the composition according to the invention may be about 0.05 to about 8 wt %, about 0.1 to about 7 wt %, about 0.5 to about 6 wt %, about 0.5 to about 5 wt %, about 1 to about 5 wt %, about 1.5 to about 4 wt %, or about 2 to about 3 wt %, based on the total weight of the composition.

In addition, the compositions according to the invention may comprise a suitable carrier. The carrier in the compositions according to the invention is selected from pharmaceutically acceptable carriers conventionally used in the art for the preparation of compositions and dressings for wound treatment. In some embodiments, the carrier in the composition according to the invention may be an aqueous carrier, preferably water. In a preferred embodiment, the carrier also exhibits antiseptic properties. For example, in one embodiment, an aqueous solution of sodium hypochlorite is used as a carrier in the compositions of the present invention. The concentration of the sodium hypochlorite solution can be selected by a person skilled in the art on the basis of the information available in the prior art (see, for example, the Order of Ministry of Health of the Russian Federation no. 178 of Jun. 20, 1995, registration No. 95/178/10; The guideline for using EDO solution is approved by the Pharmacological Committee of the Ministry of Health of the Russian Federation on Apr. 12, 1995). For example, the concentration of the sodium hypochlorite solution used to prepare the compositions according to the invention may be in the range of 0.01-1 wt %. In particular, such a solution can have a concentration of 0.06 wt % conventionally used in the field of medicine for disinfection, or a concentration of 0.1 wt %.

The compositions according to the invention may also comprise other auxiliary components selected from those conventionally used in the art. Such auxiliary components may be, for example, additional pharmaceutical agents, wetting agents, surfactants, viscosity modifiers, stabilizers, substances promoting tissue regeneration and growth, cytokines, vitamin K, fibrinogen, thrombin, factor VII, factor VIII, colorants, flavoring agents and the like. In one embodiment, such an auxiliary component can be, for example, glycerol.

Suitable amounts of such auxiliary components can be determined by a person skilled in the art based on the general knowledge and the prior art. For example, the auxiliary components may be present in the composition according to the invention in an amount of 20 wt % or less, for example 10 wt % or less, 5 wt % or less, 2.5 wt % or less, 2 wt % or less, 1.5 wt % or less, 1 wt % or less, 0.5 wt % or less, or even 0.1 wt % or less.

A composition according to the invention can be prepared by mixing the ingredients of the composition in a suitable pharmaceutically acceptable carrier. In a preferred embodiment, the compositions according to the invention are in the form of an amorphous gel.

In one embodiment, to produce a composition according to the invention, a collagen hydrolysate, an alginic acid salt, antiseptics, unithiol and dimethylsulfoxide can be dissolved in a pharmaceutically acceptable carrier at room temperature under stirring conditions. The order of the components addition is not limited in any particular way and can be selected by a skilled person based on the practical usability reasoning.

The prepared composition according to the invention may be applied to a wound surface. According to the present invention, the composition may be applied in one or more layers using methods conventionally used in the art. If necessary, the conventional means used in the art for this purpose may be used to apply the composition, such as, for example, sterile wipes, syringes, spatulas, and the like.

The application of the composition may be preceded by a primary wound treatment, which is aimed at stopping the bleeding, cleaning the wound, infection prevention, and the like.

In addition, the composition according to the invention may be applied to the wound during or after the completion of a surgical operation, for example immediately before or after suturing the wound.

If necessary, the applied composition may be additionally fixed on the wound surface using conventional means used in the art for this purpose, such as, for example, a sterile gauze dressing and the like.

The composition applied to a wound surface is a biodegradable film which, if necessary, may easily be removed by water or saline.

The invention will now be illustrated using specific exemplary embodiments. These examples are not intended to limit the scope of the invention and are intended solely for illustrating the main principles of the present invention. Specific features disclosed in the examples are not to be construed as limiting the scope of the invention by these specific features. On the contrary, it should be appreciated by one skilled in the art that the specific features of the invention illustrated in the examples are just several of the preferred and yet simple and clear embodiments of the general principles on which the claimed invention is based, said embodiments intended to help a skilled person in understanding the scope of the claimed invention in its entirety as defined in the appended claims.

Examples

The antitoxic and anesthetic effect of the antiseptic gel according to the invention was studied in white outbred male rats weighing 220-280 g (see "Experimental Toxicology" ed. by Sofronov G. A., Shilova V. V., St. Petersburg: Medkniga "ELBI-SPb", 2011, p. 272; this document is included in its entirety in the present document by reference).

Five series of experiments were carried out on 10 rats in each series, on a model of a recent wound contaminated with Staphylococcus aureus 209 P "Oxford" at a dose of $10^9$ CFU/$cm^2$.

In the first series of experiments composition "ARGAKOL" was investigated, said composition being the closest analog of the invention—adhesive corresponding to RU 2284824 and having the following composition:

| Ingredients | Wt % |
| --- | --- |
| Collagen hydrolysate "Belkozin" type A (powder, 100%) | 50 |
| Sodium alginate | 4 |
| Benzalkonium chloride 100% | 0.15 |
| Poviargol | 2 |
| Dioxidine | 2 |
| Glycerol | 2.5 |
| Methylparaben | 0.1 |
| Propylparaben | 0.05 |
| Aqueous solution of sodium hypochlorite 0.1% (1000 mg/l) | Up to 100 |

In the second series of experiments, composition "ARGAKOL-L" was investigated, corresponding to "ARGAKOL" composition from the first series of experiments and additionally comprising 2 wt % of lidocaine and 0.5 wt % of dimethylsulfoxide:

| Ingredients | Wt % |
| --- | --- |
| Fish collagen hydrolysate (powder 100%) | 50 |
| Sodium alginate | 4 |
| Benzalkonium chloride 100% | 0.15 |
| Poviargol | 2 |
| Dioxidine | 2 |
| Glycerol | 2.5 |
| Dimethylsulfoxide | 0.5 |
| Lidocaine | 2 |
| Methylparaben | 0.1 |
| Propylparaben | 0.05 |
| Aqueous solution of sodium hypochlorite 0.1% (1000 mg/l) | Up to 100 |

In the third series of experiments, composition "ARGA-KOL-U-3" was investigated, corresponding to "ARGA-KOL" composition from the first series of experiments and additionally comprising 3 wt % of unithiol and 0.5 wt % of dimethylsulfoxide:

| Ingredients | Wt % |
| --- | --- |
| Fish collagen hydrolysate (powder 100%) | 50 |
| Sodium alginate | 4 |
| Benzalkonium chloride 100% | 0.15 |
| Poviargol | 2 |
| Dioxidine | 2 |
| Glycerol | 2.5 |
| Dimethylsulfoxide | 0.5 |
| Unithiol | 3 |
| Methylparaben | 0.1 |
| Propylparaben | 0.05 |
| Aqueous solution of sodium hypochlorite 0.1% (1000 mg/l) | Up to 100 |

In the fourth series of experiments, composition "ARGA-KOL-U-5" was investigated, corresponding to "ARGA-KOL" composition from the first series of experiments and additionally comprising 5 wt % of unithiol and 0.5 wt % of dimethylsulfoxide:

| Ingredients | Wt % |
| --- | --- |
| Fish collagen hydrolysate (powder 100%) | 50 |
| Sodium alginate | 4 |
| Benzalkonium chloride 100% | 0.15 |
| Poviargol | 2 |
| Dioxidine | 2 |
| Glycerol | 2.5 |
| Dimethylsulfoxide | 0.5 |
| Unithiol | 5 |
| Methylparaben | 0.1 |
| Propylparaben | 0.05 |
| Aqueous solution of sodium hypochlorite 0.1% (1000 mg/l) | Up to 100 |

In the fifth series of experiments, composition "ARGA-KOL-LU" was investigated, corresponding to "ARGAKOL-U-5" composition from the fourth series of experiments and additionally comprising 2 wt % of lidocaine:

| Ingredients | Wt % |
| --- | --- |
| Fish collagen hydrolysate (powder 100%) | 50 |
| Sodium alginate | 4 |
| Benzalkonium chloride 100% | 0.15 |
| Poviargol | 2 |
| Dioxidine | 2 |
| Glycerol | 2.5 |
| Dimethylsulfoxide | 0.5 |
| Lidocaine | 2 |
| Unithiol | 5 |
| Methylparaben | 0.1 |
| Propylparaben | 0.05 |
| Aqueous solution of sodium hypochlorite 0.1% (1000 mg/l) | Up to 100 |

Each composition was prepared by sequential dissolving and mixing of the ingredients in a 0.1% solution of sodium hypochlorite at room temperature. The method for preparing the claimed compositions and the method for obtaining the closest analog adhesive were essentially the same. In a solution of sodium hypochlorite, the following was dissolved successively: collagen hydrolysate, sodium alginate, benzalkonium chloride, poviargol, glycerol, dimethylsulfoxide, dioxidine, methylparaben, propylparaben, and, if used, lidocaine and unithiol. The components were mixed with a laboratory anchor agitator. The prepared compositions were a gel.

When applied to a wound surface, the compositions according to the invention formed elastic biodegradable films on the wound surface which, in their mechanical properties, were similar to the films obtained according to RU 2284824. The compositions according to the invention showed a good adhesion to the skin and tissues and ensured fixation of dressings on the skin surface around the wounds.

In each series of experiments, two symmetrical wounds were made on the back (between the shoulder blades) of each rat under anesthesia using a tubular punch with a cutting edge diameter of 10 mm. Both wounds were infected (with strain *Staphylococcus aureus* 209 P "Oxford") at a dose of $10^9$ $CFU/cm^2$ and immediately filled with corresponding composition and fixed with a sterile gauze dressing. An experimental study of the antitoxic and anesthetic effect was made using standard methods for assessing behavior and motor function of animals: by studying "vertical" motor activity in a confined space; using the method of an open area ("hole-board test"); "open field test" (MR 2166-80, "Methodological recommendations on the use of behavioral reactions of animals in toxicological studies for the purposes of hygienic rationing", 1980, published in Russian language). The evaluation was performed daily from the moment of the operation for 3 days, with the first day of the study being started 6 hours after the wounds were made and the bandages were fixed.

The determination of the "vertical" motor component of the orienting reaction is based on the calculation of the number of the animals standing on the hind legs (upright posture in rats) in a confined space—in an installation of 400 mm high, 200 mm in diameter, for a predefined time of 1 minute. The normal result for male rats is 5.6±0.65.

In the "hole-board test", the rat is placed in the center of a horizontally mounted platform having a size of 60×60 cm, in which there are 16 evenly spaced holes with a diameter of 4 cm. The height of the platform is 20 cm. For 3 minutes, the number of animal looks into the holes is visually counted. The normal result for male rats is 8.5±0.75.

The "open field test" is based on the evaluation of horizontal activity of rats in an arena, in a darkened room. Observation of animals is carried out strictly at the same time of day for 2 minutes with a constant local illumination of the arena during the experiment with a 500 W lamp with a mirror reflector. The floor of the arena is separated with black lines into 16 squares (sectors) having a size of 20×20 cm. The number of squares crossed (by 4 paws) during the spontaneous horizontal movement of the animal is visually counted and the distance in meters is calculated according to the formula:

$$i = k \times n, \text{ where}$$

i—length of run in meters;
k—conversion factor 0.15 (calculated on the basis of the size and number of the squares);
n—the number of squares crossed during the movement.

The normal result for male rats is 5.21±0.29 m.
The results of the studies are provided in Table 1.

TABLE 1

Results of the assessment of the behavior and motor function of male rats during the treatment of infected wounds with antiseptic compositions in conditions of microbial intoxication.

| Parameter | Normal value | "ARGAKOL" | | | "ARGAKOL-L" comprising lidocaine | | | "ARGAKOL-U-3" comprising 3% of unithiol | | | "ARGAKOL-U-5" comprising 5% of unithiol | | | "ARGAKOL-LU" comprising lidocaine and 5% of unithiol | | |
|---|---|---|---|---|---|---|---|---|---|---|---|---|---|---|---|---|
| | | day 1 | day 2 | day 3 | day 1 | day 2 | day 3 | day 1 | day 2 | day 3 | day 1 | day 2 | day 3 | 1 day | 2 day | 3 day |
| "Vertical" motor activity in a confined space | 5.6 ± 0.65 | 0 | 1.1 | 1.9 | 1.9 | 3.0 | 3.9 | 1.8 | 2.9 | 3.8 | 3.7 | 4.8 | 4.9 | 3.8 | 4.9 | 5.0 |
| "Open-area" method ("hole-board test") | 8.5 ± 0.75 | 1.1 | 1.9 | 3.9 | 1.9 | 4.1 | 5.9 | 1.8 | 3.9 | 5.8 | 3.9 | 5.9 | 7.8 | 4.1 | 6.1 | 7.9 |
| "Open field test", "horizontal" motor activity | 5.21 + 0.29 m | 0 | 0.88 | 1.08 | 0.98 | 1.93 | 2.94 | 1.01 | 1.88 | 2.90 | 1.91 | 3.93 | 4.92 | 1.95 | 4.05 | 5.04 |

As one can see from the above table, the animals treated with "ARGACOL" composition were immobile during the observation time in the 1st day after the operation, did not show any vertical and horizontal activity. In the 2nd and 3rd day after the operation, the animals exhibited a vertical activity that was 5.1 and 2.9 times below the normal values, respectively.

When using the composition "ARGAKOL-L" with lidocaine, the motor activity of the animals was observed in the experiment 6 hours after the operation, the number of upright postures in rats being 2.9 times lower that the normal value on the 1st day, 1.9 times lower that the normal value on the 2nd day, 1.4 times lower that the normal value on the 3rd day.

In the group where "ARGAKOL-U-3" composition comprising unithiol was used, the number of upright postures in rats was 3.1 times lower than the normal value on the 1st day, 1.9 times lower than the normal value on the 2nd day, 1.5 times lower than the normal value on the 3rd day.

In groups, where composition "ARGAKOL-U-5" comprising unithiol and composition "ARGAKOL-LU" comprising lidocaine and unithiol were used, the vertical activity parameter was better in all observation times compared to the previous groups, and it reached the normal range on the 3rd day (the differences were insignificant, $P>0.05$).

On the 2nd and 3rd days after the operation, the animals treated with "ARGAKOL" composition showed a horizontal activity, but it was 5.9 and 4.8 times lower than the normal value, respectively.

When composition "ARGAKOL-L" comprising lidocaine was used, the horizontal activity of the animals was 5.3 times lower than the normal value on the first day, 2.7 times lower than the normal value on the 2nd day, 1.8 times lower than the normal value on the third day.

In the group, where composition "ARGAKOL-U-3" comprising unithiol was used, the horizontal activity in rats was 5.1 times lower than the normal value on the first day, 2.8 times lower than the normal value on the 2nd day, 1.8 times lower than the normal value on the 3rd day.

In the groups, where composition "ARGAKOL-U-5" comprising unithiol and composition "ARGAKOL-LU" comprising lidocaine and unithiol were used, the horizontal activity was better than in the previous groups in all observation times, and it reached the normal range on the 3rd day (the differences were insignificant, $P>0.05$).

In the group of animals treated with "ARGAKOL" composition, the number of looks into the holes was 7.7 times lower than the normal value on the first day of the observation, it was 4.5 times lower than the normal value on the 2nd day, and it was 2.2 times lower than the normal value on the 3rd day.

When using composition "ARGKOL-L" comprising lidocaine, the number of looks into the holes by the animals was 4.5 times lower than the normal value on the first day, 2.1 times lower than the normal value on the 2nd day, and 1.4 lower than the normal value on the 3rd day.

When using the composition "ARGAKOL-U-3" with a unithiol, the indices of hole-board test of animals were 4.7 times less than the normal in the first day, 2.2 times in the second day, 1.5 times in the third day.

In the groups where composition "ARGAKOL-U-5" comprising unithiol and composition "ARGAKOL-LU" comprising lidocaine and unithiol were used, the explorative activity was better than in the previous groups in all observation times, and it reached the normal range on the 3rd day (the differences were insignificant, $P>0.05$).

As one can see from the obtained results, the composition according to the invention comprising 3 wt % of unithiol and 0.5 wt % of dimethylsulfoxide was significantly more effective than the composition according to RU 2284824. The addition of a combination of unithiol and dimethylsulfoxide to the known composition unexpectedly led to a significant improvement in the condition of the tested animals, as evidenced by increased values of motor activity. It is important to note that the motor activity values observed in the case of using "ARGAKOL-U-3" composition were close to those observed in the case of using "ARGAKOL-L" composition, i.e. the known composition added with 0.5 wt % of dimethylsulfoxide and 2 wt % of a well-known anesthetic (lidocaine). Thus, the detoxication effect of unithiol, when used in amount of 3% in a composition for topical application to the wound surface, with respect to the motor activity of the animals, provides an effect comparable to the direct anesthetic effect of lidocaine. Such a high efficiency of unithiol in the compositions according to the invention is highly unexpected.

Moreover, an increase in the concentration of unithiol in the composition according to the invention to 5 wt % led to an even more significant improvement in the condition of the tested animals, so that on the third day of observation the rat's motor activity was almost normal. From the above data, it also follows that in the above experiments, an addition of lidocaine to composition "ARGAKOL-U-5" comprising 5% of unithiol did not result in any significant improvement of results, which proves a rapid healing process in the tested rats when using composition "ARGAKOL-U-5" and which can probably be explained by the absence of substantial painful sensations in the animals that could be suppressed by lidocaine in this case.

Also, the inventors investigated dynamics of wound contamination with a test strain of *Staphylococcus aureus*.

To quantify the number of bacteria in 1 ml of biosubstrate, the method of sectoral inoculations was used ("Manual on Medical Microbiology. General and Sanitary Microbiology. Book I", edited by Labinskaya A. S., Volina E. G. M.: BINOM Publishing, 2008, p. 1080, published in Russian language; this document is incorporated therein by reference in its entirety). To this end, a wound content was collected using a standard calibrated bacteriological loop (diameter 2 mm, capacity 0.005 ml). The collected wound content was put in 1 ml of sterile saline. Then, the same loop was used to seed the test material on sector A of a Petri dish with a simple agar, making about 40 streaks. Then, the loop was annealed and 4 streak inoculations were made from sector A to sector I, from sector I to sector II, and from sector II to sector III, the loop was annealed after each step. The plates were incubated at 37° C. for 18 to 24 hours, after that the number of colonies growing in different sectors was counted and the number of bacteria in 1 ml was determined based on the table provided in the cited document.

On the 3rd day of observation after removal of the bandage with "ARGACOL" gel, microbial contamination of the wounds in the experimental animals described above was $10^5$ CFU/cm$^2$. In the case of "ARGAKOL-L" and "ARGAKOL-U-3" compositions, contamination of the wounds in animals was $10^5$ CFU/cm$^2$ too, but in the case of "ARGAKOL-U-5" and "ARGAKOL-LU" compositions, it was $10^4$ CFU/cm$^2$.

Thus, one can conclude that the use of unithiol at a concentration of 5 wt % and higher in combination with dimethylsulfoxide unexpectedly leads to an accelerated wound healing, as evidenced, in particular, by a decrease in the microbial contamination of the wound by an order to magnitude in comparison with other investigated compositions.

The invention claimed is:

1. A composition for wound treatment comprising a collagen hydrolysate in the amount from 50 to 80 wt %, one or more pharmaceutically acceptable salts of alginic acid in the amount from 3 to 5 wt %, one or more antiseptics in the amount from 0.01 to 20 wt %, wherein the one or more antiseptics comprises a combination of dioxidine, benzalkonium chloride, poviargol, methylparaben, propylparaben, and glycerol; unithiol in the amount from 3 to 5 wt %, dimethylsulfoxide in the amount from 0.5 to 2 wt % and a pharmaceutically acceptable aqueous carrier.

2. The composition according to claim 1, further comprising one or more anesthetics.

3. The composition according to claim 2, wherein one or more of the anesthetics is selected from the group consisting of lidocaine, trimecaine, tetracaine, novocaine and a combination thereof.

4. The composition according to claim 3, wherein the amount of one or more anesthetics is about 0.01 to about 10 wt % based on the total weight of the composition.

5. The composition according to claim 1, wherein the pharmaceutically acceptable carrier includes an aqueous solution of sodium hypochlorite.

6. The composition according to claim 1, wherein:
the amount of dioxidine is about 0.1 to about 10 wt % based on the total weight of the composition;
the amount of poviargol is about 0.1 to about 10 wt % based on the total weight of the composition;
the amount of benzalkonium chloride is about 0.01 to about 2 wt % based on the total weight of the composition;
the amount of glycerol is about 0.1 to about 15 w % based on the total weight of the composition;
the amount of methylparaben is about 0.001 to about 2 wt % based on the total weight of the composition; and
the amount of propylparaben is about 0.001 to about 2 wt % based on the total weight of the composition.

7. The composition according to claim 1, wherein one or more salts of alginic acid are selected from the group consisting of sodium, potassium, calcium salts of alginic acid and a combination thereof.

8. The composition according to claim 1, additionally comprising auxiliary components selected from the group consisting of pharmaceutical agents, wetting agents, surfactants, viscosity modifiers, stabilizers, substances promoting tissue regeneration and growth, cytokines, vitamin K, fibrinogen, thrombin, factor VII, factor VIII, colorants and flavoring agents.

9. The composition according to claim 8, wherein said auxiliary components are present in the composition in an amount of 20 wt % or less.

10. The composition according to claim 1 for use in wound treatment.

* * * * *